US 6,696,243 B2

(12) United States Patent
Siiman (10) Patent No.: US 6,696,243 B2
(45) Date of Patent: Feb. 24, 2004

(54) METHOD FOR THE ANALYSIS OF SOLUBLE ANALYTES

(75) Inventor: Olavi Siiman, Davie, FL (US)

(73) Assignee: Coulter International Corp., Miami, FL (US)

( * ) Notice: Subject to any disclaimer, the term of this patent is extended or adjusted under 35 U.S.C. 154(b) by 89 days.

(21) Appl. No.: 09/768,127

(22) Filed: Jan. 23, 2001

(65) Prior Publication Data

US 2002/0142289 A1 Oct. 3, 2002

(51) Int. Cl.[7] .................... G01N 33/533; C12Q 1/70
(52) U.S. Cl. .................... 435/5; 435/7.24; 435/7.21; 435/7.32; 435/7.93; 435/968; 436/63; 436/64; 436/529; 436/547; 436/850; 436/512
(58) Field of Search .................... 435/5, 7.24, 7.21, 435/7.32, 7.93, 968; 436/63, 64, 529, 547, 800, 512, 513

(56) References Cited

U.S. PATENT DOCUMENTS

| | | |
|---|---|---|
| 4,542,104 A | 9/1985 | Stryer et al. |
| 4,931,395 A | 6/1990 | Griffin |
| 5,171,846 A | 12/1992 | Gupta |
| 5,240,640 A | 8/1993 | Siiman et al. |
| 5,248,772 A | 9/1993 | Siiman et al. |
| 5,262,302 A | 11/1993 | Russell |
| 5,272,257 A | 12/1993 | Gupta |
| 5,466,609 A | 11/1995 | Siiman et al. |
| 5,527,713 A | 6/1996 | Bolton et al. |
| 5,552,086 A | 9/1996 | Siiman et al. |
| 5,639,620 A | 6/1997 | Siiman et al. |
| 5,658,741 A | 8/1997 | Bolton et al. |
| 5,707,877 A | 1/1998 | Siiman et al. |
| 5,776,706 A | 7/1998 | Siiman et al. |
| 5,814,468 A | 9/1998 | Siiman et al. |
| 5,891,741 A * | 4/1999 | Siiman et al. ............ 436/529 |
| 5,945,293 A | 8/1999 | Siiman et al. |
| 5,994,089 A * | 11/1999 | Siiman et al. ............ 435/7.24 |
| 6,074,884 A | 6/2000 | Siiman et al. |

OTHER PUBLICATIONS

7th Workshop and Conference on Human Leukocyte Differentiation Antigens, Harrogate, Jun. 2000.
Custer, M.C. and Lotze, M.T., *J. Immunol. Meth.*, 128, 109–117 (1990).
Delaire, S. et al, *Cell. Mol. Life Sci.*, 54:1265–1276 (1998).
Ferguson, M.A.J., *J. Cell. Sci.*, 112:2799–2808 (1999).
Fischer, M.B., et al, *Nature*, 408:479–483 (2000).
Fleit, H.B., et al, *Blood*, 79:2721–2728 (1992).
Galon, J., et al, *J. Immunol.*, 157: 1184–1192 (1996).
Herold, C., et al, *Leukocyte Typing* V, 288–292 (1995).

(List continued on next page.)

*Primary Examiner*—Long V. Le
*Assistant Examiner*—Changhwa J Cheu
(74) *Attorney, Agent, or Firm*—Howson and Howson; Mitchell E. Altor (57) ABSTRACT

A method of analyzing the concentration of soluble analyte in a sample involves performing a competition assay using a predetermined amount of formed bodies to which are attached at least one analyte, varying known concentrations of an unlabeled ligand that binds to analyte, and a known concentration of ligand labeled with a detectable marker. After analysis in a flow cytometer, the test sample and a plurality of control samples generate data on curves formed by plotting signal vs. concentration of labeled ligand in controls (first), and vs. concentration of total labeled and unlabeled ligand in test samples (second). The concentration of unlabeled ligand that bound to soluble analytes in test samples is determined by evaluating the difference between the concentration that corresponds with the intersection of these two curves and the constant labeled ligand concentration in the test samples. The concentration of said soluble analytes in said sample is the product of that difference and the binding stoichiometry of the ligand to soluble analytes.

23 Claims, 4 Drawing Sheets

OTHER PUBLICATIONS

Huizinga, T.W.J., et al, *J. Clin. Invest.,* 86: 416–423 (1990).
Kindzelskii, A.L., et al, *J. Immunol.,* 164: 953–958 (2000).
Kohler, G. and Milstein, C., *Nature,* 256: 495–497 (1975).
Kuijpers, T.W., et al, *J. Immunol. Meth.,* 232: 211–229 (1999).
Roederer, M., et al, *Cytometry,* 24:191–197 (1996).
Siiman, O. and Burshteyn, A., *Cytometry,* 40: 316–326 (2000).
Siiman, O., et al, "Covalently Bound Antibody on Polystyrene Latex Beads: Formation, Stability and Use in Analyses of White Blood Cell Populations", *J. Colloid Interface Sci.,* 234: (Feb. 2001).
Siiman, O. and Burshteyn, A., *J. Phys. Chem.,* 104:9795–9810 (2000).
Siiman, O., et al, *Cytometry,* 41:298–307 (2000).
Stahl, N., et al, *Cell,* 51:229–240 (1987).
Teillaud, J. L., et al, *Immunomethods,* 4: 48–64 (1994).
Tosi, M. F. and Zakem, H., *J. Clin. Invest.,* 90: 462–470 (1992).
Van Eeden, S.F., et al, *J. Immunol. Meth.,* 232: 23–43 (1999).
Waggoner, A.S., et al, *Ann. N.Y. Acad. Sci.,* 677:185–193 (1993).

* cited by examiner

Control (whole blood + no unlabeled Ab /standard non-saturating amt. of labeled Ab)

antigens    soluble
on cell     antigen

FIG. 1A

Competitive Binding (whole blood + low unlabeled Ab titer/standard labeled Ab)

FIG. 1B

Competitive Binding (whole blood + low-medium unlabeled Ab titer/standard labeled Ab)

FIG. 1C

Competitive Binding (whole blood + medium unlabeled Ab titer/standard labeled Ab)

METHOD FOR THE ANALYSIS OF SOLUBLE ANALYTES

BACKGROUND OF THE INVENTION

The present invention relates to improved methods for the identification and quantification of soluble analytes in a sample. More particularly, the present invention relates to a simple rapid flow cytometric method of such analysis.

Simple methods for the analysis and quantification of soluble analytes in a sample, for which analytes specifically binding ligands exist, are useful in a wide variety of applications. Medical applications such as diagnosis of diseases characterized by the presence of certain analytes in a biological sample or the evaluation of commercial or industrial samples containing analytes can be accomplished with such methods. For example, methods for the analysis of soluble analytes, such as antigenic receptors which are shed from their normal positions on the surfaces of formed bodies, particularly cells, can provide information essential to the diagnosis of disease states and the monitoring of the efficacy of treatment of various diseases.

Conventional methods for such analysis included steps such as equilibration of a labeled ligand with a cell suspension, followed by a separation (e.g., wash) of bound from unbound ligands to obtain the solution concentration of ligand. Thereafter graphical analysis employing a set of cell-bound, labeled ligands, fluorescence intensities and the solution concentration of labeled ligand, produced the necessary data for analysis. Other known methods for the analysis of receptors employed differently labeled ligands, external standards for calibration, or image analysis.

Flow cytometry methods were recently used to analyze quantitatively for shed antigenic receptor in solution in a competitive binding experiment that used both unlabeled and labeled ligand with unknown amounts of bound and shed antigen without a separation step or an external standard [Siiman, O. and Burshteyn, A., *Cytometry*, 40: 316–326 (2000); and U.S. Pat. No. 5,814,468, both incorporated herein by reference]. Briefly described, this method obtained the amount of soluble antigenic receptor in a sample that contained unknown amounts of soluble (i.e., shed) antigenic receptor and cell-surface bound antigenic receptor. The method combined the data from a number of assay steps. In the first assay step, a control sample containing only labeled ligand was mixed and equilibrated with a fixed number of cells in whole blood. In a second step, a competition test sample containing both labeled and unlabeled ligand were mixed sequentially and equilibrated with a fixed number of cells in whole blood. In both steps, the cells were fixed by lysing the red blood cells and quenching (Q-PREPing) them. The cells were run on a conventional flow cytometer. The results were analyzed by determining the unlabeled ligand concentration at which the fluorescence intensity of the labeled ligand in the competitive binding assay using variable titers of unlabeled ligand and fixed titers of labeled ligand matches the fluorescence intensity of the control with no unlabeled ligand. This method permitted an estimation of the concentration of soluble antigenic receptor in blood plasma.

Additional or modified methods for analysis of such bound and shed antigenic receptors are needed for other purposes, such as the measurement of certain antigenic receptors on neutrophils, which have some unusual functions [Edwards S W, "*Biochemistry and physiology of the neutrophil*", Cambridge, UK: Cambridge, University Press; (1994); Abramson J S, and Wheeler J G, eds, "*The neutrophil.*" Oxford, UK: IRL Press at Oxford University Press (1993)]. For example, the quantification of the shedding of the Fcγ receptor III on neutrophils in whole blood has thus far been done using a long and tedious ELISA method. Controls are not easily obtained for the ELISA assay.

For example, the Fcγ receptor IIIB is anchored to the neutrophil membrane via a glycosyl-phosphatidylinositol (GPI) linkage through a terminal serine residue. This linkage can be easily cleaved by enzymes such as elastase and pronase or activation by certain stimuli such as the chemotactic peptide, N-formyl-MET-LEU-PHE, and phorbol myristate acetate (PMA), which induce shedding of Fcγ RIIIB from the neutrophil surface [Huizinga T. W. J. et al, *J. Clin. Invest.*, 86: 416–423 (1990); Tosi, M. F. and Zakem, H., *J. Clin. Invest.*, 90: 462–470 (1992)]. Soluble Fcγ RIIIB in normal human serum was detected in widely variable concentrations ranging from 7.3 to 75.9 nmol/L [Fleit H. B., et al, *Blood*, 79:2721–2728 (1992)] with the monoclonal antibodies, CLBFcRgran 1, BW209/2, and 3G8 or 3G8 Fab.

Thus, there remains a need in the art for additional and modified, flow cytometric methods of analysis for soluble analyte in a sample.

BRIEF SUMMARY OF THE INVENTION

In one aspect, the present invention provides a method of analyzing the concentration or amount of soluble analyte in a sample. The method involves the steps of adding to a series of test samples containing an unknown concentration of soluble analyte: a predetermined amount of formed bodies to which are attached at least one analyte, varying known concentrations of an unlabeled ligand that binds to said analyte, and a known concentration of said ligand labeled with a detectable marker. Preferably, the analytes are covalently attached to the formed bodies and a constant known concentration of the ligand labeled with a detectable marker is used. The samples are incubated and labeled ligand and the unlabeled ligand compete for binding to the formed body-bound analyte and the soluble analyte. The control samples contain the sample with an unknown concentration of soluble analyte, the predetermined amount of the formed bodies, and varying known concentrations of the labeled ligand with no unlabeled ligand. All control samples are incubated to achieve equilibrium binding of ligand to analyte from about 1% occupation of binding sites on analytes bound to the formed bodies to 100% occupation at saturation, i.e., labeled ligand binds to the formed body-bound analytes and the soluble analyte. Each test sample and control sample is analyzed by an instrument that measures detectable signal produced from the labeled ligands bound to the bound analytes on the formed bodies. Thereafter, the intersection of a curve formed by plotting the signal against the concentration of the labeled ligand in the control samples, and a second curve formed by plotting the signal against the concentration of total labeled and unlabeled ligand in the test samples is identified. Preferably, the curve is a linear—log graphical dependence curve and the concentration is a molar concentration. The concentration of unlabeled ligand that bound to soluble analytes in the test samples is determined by evaluating the difference D between the molar concentration that corresponds with the intersection and the constant labeled ligand concentration in the test samples. The concentration of the soluble analytes in the sample is obtained by determining the product of the value D and the binding stoichiometry of the ligand to soluble analytes.

In another aspect, the present invention provides a method of analyzing the concentration or amount of soluble receptors in a sample, wherein the sample comprises formed bodies having the receptors bound thereto and the soluble receptors shed from the formed bodies. The method involves incubating a series of test samples containing a predetermined amount of the formed bodies, varying known concentrations of a ligand that binds to the receptor, and a known concentration of the ligand labeled with a detectable marker. Preferably, a constant known concentration of the ligand labeled with a detectable marker is used. The labeled ligand and the unlabeled ligand compete for binding to the bound and soluble receptors. Control samples contain the sample with an unknown concentration of soluble analyte, the predetermined amount of the formed bodies, and varying known concentrations of the labeled ligand with no unlabeled ligand. All control samples are incubated to achieve equilibrium binding from about 1% occupation of binding sites on formed bodies to 100% occupation at saturation, i.e., labeled ligand binds to the formed body-bound analytes and the soluble analyte. Each test sample and control sample is analyzed in an instrument that measures detectable signal produced from the labeled ligands bound to the bound receptors on the formed bodies. The intersection of a curve formed by plotting the signal against the concentration of the labeled ligand in the control samples, and a second curve formed by plotting the signal against the concentration of total labeled and unlabeled ligand in the test samples is identified. Preferably, the curve is a linear—log graphical dependence curve and the concentration is a molar concentration. The concentration of soluble receptors released from the formed bodies is thereafter determined by evaluating the difference between the concentration that corresponds with the intersection and the constant labeled ligand concentration in the test samples with the binding stoichiometry of the ligand.

In still another aspect, the invention provides a method of diagnosing a disease characterized by an altered level of soluble analyte a biological sample, e.g., blood, serum, tissue, of a mammal. The method involves analyzing the amount of soluble analyte by performing the steps of the above-described method, and comparing the concentration of soluble analyte from the mammal's samples with known normal concentrations of soluble analyte in samples from a healthy mammal, wherein a difference between the concentration of the soluble analyte in the test mammal's sample and the normal concentrations is indicative of disease.

In yet another aspect, the invention provides a method for diagnosing a disease characterized by an altered level of receptors shed by target cells into the blood of a mammal comprising the steps of analyzing the amount of soluble receptor shed from the surface of the target cells into the mammalian blood sample by the method described above; and comparing the concentration of soluble receptors from the mammal's samples with known normal concentrations of soluble receptors in samples of healthy mammalian blood. A significant difference between the concentration of soluble receptors in the mammal's blood sample and the normal concentrations is indicative of disease.

In another aspect, the invention provides a computer program which identifies and analyzes the amount of soluble analyte in a sample, e.g., soluble receptor shed from the surface of a formed body into solution in a sample comprising formed bodies, by implementing the above-mentioned method.

In still another aspect, the invention provides an analysis instrument that comprises an integrated computer program which identifies and analyzes the amount of soluble analyte in a sample, e.g., soluble receptor shed from the surface of a formed body into solution in a sample comprising formed bodies, by implementing the above-mentioned method.

In another aspect, the invention provides a diagnostic kit useful for the performance of these methods, particularly for diagnosis of a disease.

Other aspects and advantages of the present invention are described further in the following detailed description of the preferred embodiments thereof.

BRIEF DESCRIPTION OF THE DRAWINGS

FIG. 2 is a linear-log graphical dependence of mean channel fluorescence intensity of labeled antibody (1D3-FITC) vs:

(◊) the molar concentration of unlabeled antibody (1D3) in competitive binding run 1 (test sample);

(□) the molar concentration of unlabeled antibody (1D3) in competitive binding run 2 (test sample), (X) the molar concentration of labeled antibody (1D3-FITC) in non-competitive binding run 1 (control), and (▲) the molar concentration of total antibody (1D3+1D3-FITC) in competitive binding run 1 (test sample).

DETAILED DESCRIPTION OF THE INVENTION

The present invention provides a novel and improved method for analyzing the amount of soluble analyte present in a sample by utilizing formed bodies to which analyte is naturally or synthetically bound, and a competition assay format in which labeled and unlabeled ligand compete for the soluble and bound analyte. This analysis is accomplished by the use of flow cytometry.

A. Components Useful in the Method of this Invention

1. Formed Bodies

As described herein, the term "formed bodies" are particles to which analytes may be covalently bound, electrostatically bound or bound by hydrogen bonding, or some combination of these three interactions between atoms in molecules. These formed bodies may be bound either naturally occurring or synthetic.

For example, one subset of synthetic formed bodies are stable colloidal particles, such as polystyrene beads ranging in size from between about 0.2 to about 5.0 microns in diameter (i.e., colloidal-sized). Such polystyrene substrates or beads can contain aldehyde and/or sulfate functional groups, such as the commercially available beads, e.g., from Interfacial Dynamics Corporation, Portland Oreg. Alternatively, the polystyrene bead has an aminodextran coating over its peripheral surface and/or a colloidal-metal coating. Preferably an aminodextran coating is covalently bonded to the core substrate by covalent bonds between the free amino groups of the aminodextran and the amine-reactive functional groups of the polystyrene substrate and further by crosslinking with an agent such as glutaraldehyde. The aminodextran coating may generally be characterized as having a degree of diamine substitution in the range of $1/40$–$1/35$ (1x-aminodextran) compared to a maximum theoretical value of $1/2.5$. More preferably, the diamine substitution in the aminodextran coating is approximately $1/7$ to $1/8$ (5x-aminodextran). Analytes, particularly protein analytes, may be readily attached to these beads as is taught in the references cited below. See also, O. Siiman et al, "Covalently Bound Antibody on Polystyrene Latex Beads: Formation, Stability and Use in Analyses of White Blood Cell Populations", *J. Colloid Interface Sci.*, 234: (February 2001).

A variety of aminodextran-coated beads are described in U.S. Pat. Nos. 6,074,884; 5,945,293; and 5,658,741. Aminodextran-coated monodispersed colloidal dispersions of magnetic ferrite [U.S. Pat. No. 5,240,640], metal [U.S. Pat. No. 5,248,772], polystyrene [U.S. Pat. No. 5,466,609; U.S. Pat. No. 5,707,877; U.S. Pat. No. 5,639,620; U.S. Pat. No. 5,776,706], and polystyrene-metal [U.S. Pat. No. 5,552,086; U.S. Pat. No. 5,527,713] particles may also be employed as formed bodies according to this invention.

Another type of formed body may contain the above-described coated substrate with a layer of colloidal-sized metallic solid overlaying the aminodextran coating. Preferably this layer is uniformly dispersed over the dispersed surface of the aminodextran layer. The colloidal metal useful in forming the coated substrate is generally described as a metal which can be reduced from the ionic state to the metal(0) state by the aminodextran coating, or a metal which can form metal ions or metal ion complexes which have a reduction potential of about +0.7 volts or higher. While such metal ions may include: Ag(I), Au(III), Pd(II), Pt(II), Rh(III), Ir(III), Ru(II), Os(II), the preferred metal ions for such use are colloidal gold(III) and colloidal silver(I). Specifically, gold/silver colloid coated polystyrene-aminodextran beads, their preparation, characterization and use in analyses of subpopulations of white blood cells in whole blood have been described. See, e.g., U.S. Pat. No. 5,248,772; U.S. Pat. No. 5,552,086; U.S. Pat. No. 5,945,293; and O. Siiman and A. Burshteyn, *J. Phys. Chem.*, 104:9795–9810 (2000); and O. Siiman et al, *Cytometry*, 41:298–307 (2000).

An alternative to this coated substrate employs carboxy-functionalized polystyrene particles as the core substrate, coated with aminodextran by EDAC coupling as described in U.S. Pat. No. 5,639,620.

Naturally-occurring formed bodies useful in this invention can also include biological cells, particularly mammalian hematological or blood cells, and also all vertebrate or invertebrate cells, insect cells, bacterial cells, parasites, yeast or fungal cells, algal or other plant cells, etc. Also included in this definition are viruses, virus-like particles, parasites, and essentially any biological colloidal particle that has on its surface a receptor or antigen (i.e., an analyte) for which there exists a counter-receptor ligand or specific binding partner. The naturally-occurring formed bodies have analyte bound on them, e.g., cells containing cell-surface or other receptors. The present invention is described specifically below using mammalian blood cells, specifically human white blood cells, as the formed bodies.

2. Samples

The "original samples" of the invention can include any sample containing soluble analyte. For example, the samples may be biological samples, including, among others, whole blood, plasma or serum, where the formed bodies are cells, particularly blood cells. Depending on the nature of the formed body, the sample may be a synthetic sample, such as a physiologically-acceptable medium for the formed bodies, e.g., saline, buffers or plant media, or some type of commercial sample containing a soluble analyte. The sample may be a synthetic sample containing particles as well as the soluble analyte. Such samples may be purified by conventional methods, such as separation by centrifugation, etc., for the handling of other samples of that type to eliminate such particles, so as to meet the above limitation. By "test sample" is meant the original sample containing the labeled and unlabeled ligands, and to which have been added and mixed any optional buffers.

3. Analytes

By "analyte" is meant a naturally occurring molecule, soluble in a selected sample, and having a "counter-ligand" that can specifically bind to the analyte. For example, a biological receptor is an analyte, i.e., an antigen or protein or a portion thereof, that is capable of binding to a ligand, e.g., an antibody. A receptor is normally located on the surface of a formed body. Receptors inside a cell or formed body are made accessible or brought to the surface by some process such as translocation, permeabilization, electroporation, etc. There are a wide and well known variety of cell-surface receptors, including receptors located on hematological cells. Some cell-surface receptors are shed into the circulating bloodstream due to disease, e.g., cancer, or in response to some adverse event, e.g., exposure to radiation.

One particular receptor is a "GPI-linked receptor", which is an antigenic receptor anchored to a white blood cell membrane via a glycosyl-phosphatidylinositol (GPI) linkage. GPI- linked antigenic receptors have been identified among the more than 200 antigens identified on the surface of white blood cells [A. N. Barclay et al, The Leukocyte Antigen Facts Book, 2nd edit., Academic Press, San Diego, Calif., publ. (1997), section II, pp. 132–593]. These include, without limitation, CD16b, CD14, CD24, CD48, CD52, CD55, CD59, CD66b, CD66c, CD73, CD87, CD90, gp42, LY-6, RT 6, and SCA-2. Most of these antigens have been shown to occur as soluble forms in normal serum. Among other GPI-linked molecules are the normal prion protein, $PrP^c$ [N. Stahl et al, *Cell*, 51:229–240 (1987)], recently classified as CD230 [$7^{th}$ Workshop and Conference on Human Leukocyte Differentiation Antigens, Harrogate, June 2000] and the glycoproteins on the surface of insect-transmitted protozoan parasites [M. A. J. Ferguson, *J. Cell. Sci.*, 112:2799–2808 (1999)].

Still other types of analyte can include soluble proteins or other molecules that are not normally bound to formed bodies. In various fields, including medical, diagnostic, industrial and commercial, there exist soluble analytes for which identification and quantification are necessary. This invention is not limited to the identity of the analyte.

4. Ligand

By "ligand" is meant a moiety or binding partner that specifically binds to the analyte. Where the analyte is a receptor normally expressed on the surface of a cell, the ligand binds to the receptor, when it is bound to the cell or when it is released or shed therefrom into solution. Where the analyte is not normally bound to a formed body, the ligand can bind to the soluble receptor or can bind to it if the analyte is synthetically covalently linked to a formed body, such as a bead. As defined herein, ligands include various agents that detect and react with one or more specific analytes. Examples of ligands within the meaning of the present invention and their analytes include, without limitation, those listed in Table 1.

TABLE 1

| LIGAND | RECEPTOR |
|---|---|
| Antibody | Antigen |
| Natural ligands: | |
| cytokine or chemokine | CK receptor |
| Hormone | Hormone receptor |
| growth factor | Growth factor receptor |
| Secondary reagents: | |
| streptavidin | Biotinylated antibody—antigen |
| Antibody | Antibody—antigen |
| Pharmaceuticals: | |
| drugs | Drug receptor |
| Solubilized natural ligands: | |
| counter-receptor | receptor |
| CTLA-4 | B7 (CD80/86) |
| Lectins (agglutinins) | Complementary carbohydrate or oligosaccharide on cell-surface glycoprotein |
| MHC-peptide complex | T cell receptor (TCR) |
| Oligonucleotide | Complementary sequences in nucleic acids, DNA or RNA |

Methods useful for construction of such ligands are known to those of skill in the art. All such ligands are characterized by the desired ability to bind the specified analyte, whether it is soluble or bound onto a population of formed bodies. In one preferred embodiment, the ligand of the invention is a component that preferentially binds to all or a portion of a cell surface receptor. Thus, a ligand useful in this embodiment of the invention may be an antibody or a functional fragment thereof capable of binding to a cell surface receptor on a WBC population. Such antibodies or fragments include polyclonal antibodies from any native source, and native or recombinant monoclonal antibodies of classes IgG, IgM, IgA, IgD, and IgE, hybrid derivatives, and fragments of antibodies including Fab, Fab' and F(ab')2, humanized or human antibodies, recombinant or synthetic constructs containing the complementarity determining regions of an antibody, an Fc antibody fragment thereof, a single chain Fv antibody fragment, a synthetic antibody or chimeric antibody construct which shares sufficient CDRs to retain functionally equivalent binding characteristics of an antibody that binds a desired cell surface receptor, and a binding fragment produced by phage display.

Monoclonal antibodies used in the examples of this invention were generally obtained by conventional hybridoma methods and purified from ascites fluid by ammonium sulfate (45%) precipitation, centrifugation and affinity chromatography using protein A. The standard process of making monoclonal antibodies is described in G. Kohler and C. Milstein, *Nature,* 256: 495–497 (1975). Of course, the particular method of making and the type of monoclonal antibody is not limited to such techniques and it is envisioned that any technique for making such antibodies is within the practice of the invention. Any ligand which can target receptor sites on, or shed from, cells may be used, since the amplification of fluorescent intensities does not depend on the density of the particular receptor sites on a cell.

Other typical ligands can include, without limitation, a lectin, a hormone, a growth factor, or a drug or synthetic chemical compound, or portions thereof that can bind the analyte. The selection of the ligand is not a limiting factor in this invention.

5. Markers

The term "markers" generally refers to molecules, preferably proteinaceous molecules, but also small chemical molecules, preferably those which enable detection by emitting a detectable signal of a particular wavelength upon excitation by a laser. Phycobiliproteins, tandem dyes, certain fluorescent proteins, small chemical molecules, and certain molecules detectable by other means can all be considered markers for flow cytometry analyses. See, e.g., the markers listed in *Handbook of Fluorescent Probes and Research Chemicals,* 6th Ed., R. P. Haugland, Molecular Probes, Inc., Eugene, Oreg. (1996).

"Phycobiliproteins" are a family of macromolecules found in red algae and blue-green algae. The biliproteins (the term "biliproteins" is equivalent to the term "phycobiliprotein") have a molecular weight of at least about 30,000 daltons, more usually at least about 40,000 daltons, and may be as high as 60,000 or more daltons usually not exceeding about 300,000 daltons. The biliproteins will normally be comprised of from 2 to 3 different subunits, where the subunits may range from about 10,000 to about 60,000 molecular weight. The biliproteins are normally employed as obtained in their natural form from a wide variety of algae and cyanobacteria.

The presence of the protein in the biliproteins provides a wide range of functional groups for conjugation to proteinaceous and non-proteinaceous molecules. Functional groups that are present include amino, thiol, and carboxyl. In some instances, it may be desirable to introduce functional groups, particularly thiol groups when the biliprotein is to be conjugated to another protein. Each phycobiliprotein molecule contains a large number of chromophores. An exemplary ligand, e.g., an antibody molecule directly labeled with fluorescein will have between 1 and 3 chromophores associated with it. An antibody molecule (for example) directly labeled by conjugation with a phycobiliprotein may have as many as 34 associated chromophores, each with an absorbance and quantum yield roughly comparable to those of fluorescein.

Examples of phycobiliproteins useful in the present invention are phycocyanin, allophycocyanin (APC), allophycocyanin B, phycoerythrin (PE) and preferably R-phycoerythrin. PE is among the brightest fluorescent dyes currently available. Conjugated to an antibody, PE has been used to detect interleukin-4 in a fluorescent plate assay and found in M. C. Custer and M. T. Lotze, *J. Immunol. Meth.,* 128, 109–117 (1990), to be the only tested fluorophore that produced adequate signal.

The tandem dyes are non-naturally occurring molecules that may be formed of a phycobiliprotein and another dye.

See, for example, U.S. Pat. No. 4,542,104 and U.S. Pat. No. 5,272,257. Examples of tandem dyes useful in the present invention are phycoerythrocyanin or PC5 (PE-Cy5, phycoerythrin-cyanin 5.1; excitation, 486–580 nm, emission, 660–680 nm) [A. S. Waggoner et al, *Ann. N.Y. Acad. Sci.*, 677 :185–193 (1993) and U.S. Pat. No. 5,171, 846] and ECD (phycoerythrin-texas red; excitation, 486–575 nm, emission, 610–635 nm) [U.S. Pat. No. 4,542, 104 and U.S. Pat. No. 5,272,257. Other known tandem dyes are PE-Cy7, APC-Cy5, and APC-Cy7 [M. Roederer et al, *Cytometry*, 24:191–197 (1996)]. Tandem dyes, PC5 and ECD, have been successfully directly conjugated to monoclonal antibodies by several methods that involve iminothiolane activation of the dye.

Still other markers which may be directly conjugated to a ligand and used with the phycobiliproteins or tandem dyes in this invention to add additional numbers of markers (labeled ligands) to the method include small molecules which upon excitation emit wavelengths of less than 550 nm. Such molecules do not overlap with the emissions of the phycobiliproteins. One example of such a marker is fluorescein isothiocyanate (FITC). Others are listed in the Handbook cited above.

Still other markers which may be employed in this method to provide additional colors are the proteins known as the green fluorescent proteins and blue fluorescent proteins; also useful may be markers which emit upon excitation by ultraviolet light.

The biliproteins and tandem dyes are commercially available from various sources including Coulter International Corporation, Miami, Fla., Molecular Probes, Inc., Eugene, Oreg. and Prozyme, Inc., San Leandro, Calif. The other markers or labels discussed above may be obtained commercially from known sources.

B. Method for Identifying and Enumerating Soluble Analytes

The following description of the method of this invention uses one specific embodiment of analyte, formed body, ligand and sample. In this embodiment, the analyte is an antigenic receptor shed from the surface of a white blood cell into solution in a sample comprising white blood cells, with unknown amounts of both cell-bound receptor and soluble receptor. The formed body is a naturally occurring cell containing the bound receptor. The sample is whole blood containing both cell-bound receptor and receptor shed into solution from the cell. The exemplary ligand is an antibody. However, as stated above, other analytes, ligands and formed bodies may be employed in the steps of this method.

According to the method of this invention, a competition assay is performed using a varied concentration of unlabeled ligand (e.g., an antibody) and a constant concentration of labeled ligand (e.g., a labeled antibody). Samples containing a predetermined or known amount or concentration of the formed bodies (e.g., targeted cells) are incubated with labeled and unlabeled ligand that binds to the receptor. The total number of formed bodies in a sample containing appropriately labeled ligand can be obtained or predetermined, for example, by running the sample on a hematology analyzer, preferably the COULTER® STKS™ or S-Plus™ counter, and if required for subsets of cells, on a flow cytometer. Depending on the nature of the formed bodies, other methods for providing samples with predetermined amount or concentrations may be selected by one of skill in the art.

In the performance of the competitive assay test samples and in the control samples, the "labeled ligand" is labeled with a detectable marker (e.g., a fluorescent marker). Each test sample for the competitive assay step contains a known constant amount or concentration of the labeled ligand and increasing, known amounts of the unlabeled ligand, which compete for binding to the bound and soluble receptors in the sample. Each sample also contains a fixed volume or concentration of the formed bodies. The concentration of labeled ligand is preferably not above but close to saturation and is maintained as a constant in each sample. The varying concentrations of unlabeled ligand in the test samples comprise a sufficient range (i.e., where enough labeled ligand is displaced so as to obtain from 0 to between 95–100% inhibition of binding between labeled ligand and receptor). The amount of incubation time for the samples with either or both the labeled and unlabeled ligand can be selected by one of skill in the art, but is generally between about 10 minutes and about 2 hours.

Control samples are also run. The control samples contain the sample with an unknown concentration of soluble analyte, the predetermined amount of the formed bodies, and varying known concentrations of the labeled ligand with no unlabeled ligand. The sample volumes remain constant. All control samples are incubated to achieve equilibrium binding of ligand to analyte from about 1% occupation of binding sites on analytes bound to the formed bodies to 100% occupation at saturation, i.e., labeled ligand binds to the formed body-bound analytes and the soluble analyte. The fluorescence intensity of the targeted formed bodies (e.g. cells) is very sensitive to changes in the low, unlabeled ligand concentration. Preferably, for optimum sensitivity, the concentration of labeled ligand in the control should be chosen so that about 80–90% of saturation of receptor sites on the formed bodies (e.g., targeted cells) is obtained.

The competitive assay has a set of test samples with a constant amount of labeled ligand and a variable amount of unlabeled ligand for a constant aliquot of sample. The control consists of a set of test samples with a variable amount of labeled ligand for the same constant aliquot of white blood sample.

Figure 1A:
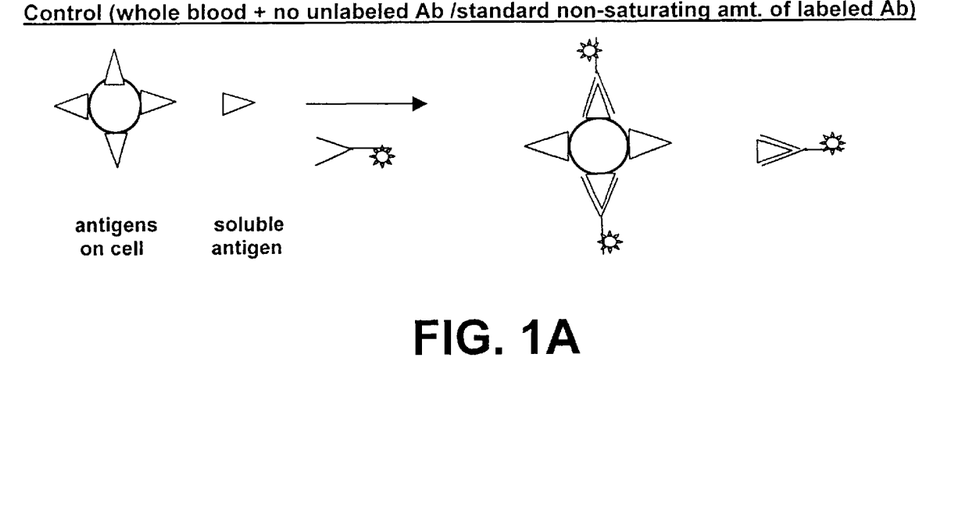
FIG. 1A is a schematic diagram showing the control of the method of this invention, which consists of a whole blood or plasma sample containing receptors (antigens) present on a cell and soluble (shed) receptors. In the presence of labeled antibody, both the receptors on the targeted cells and soluble receptors are labeled.
Figure 1B:
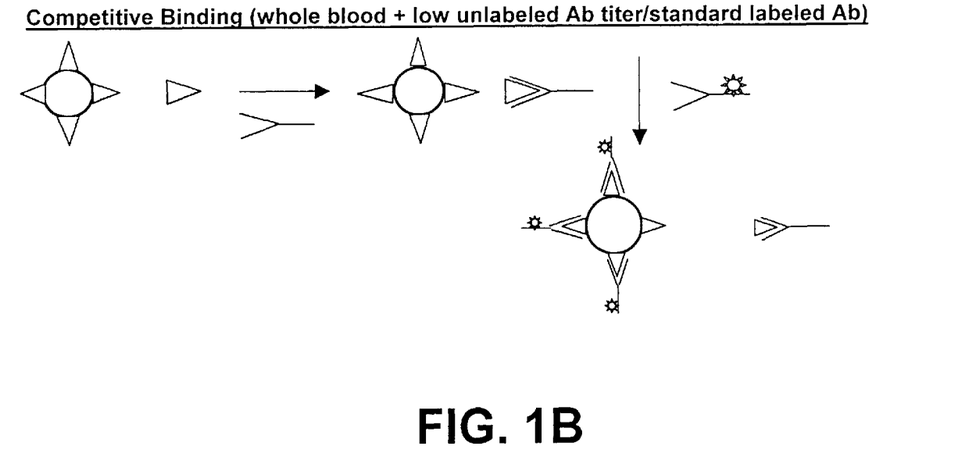
FIG. 1B is a schematic diagram showing competitive binding that occurs when the blood sample containing cell-bound receptors and soluble receptors is contacted with a low titer of unlabeled antibody, which tends to label the soluble receptors and a standard (known) titer of labeled antibody, which labels the bound receptors.
Figure 1C:
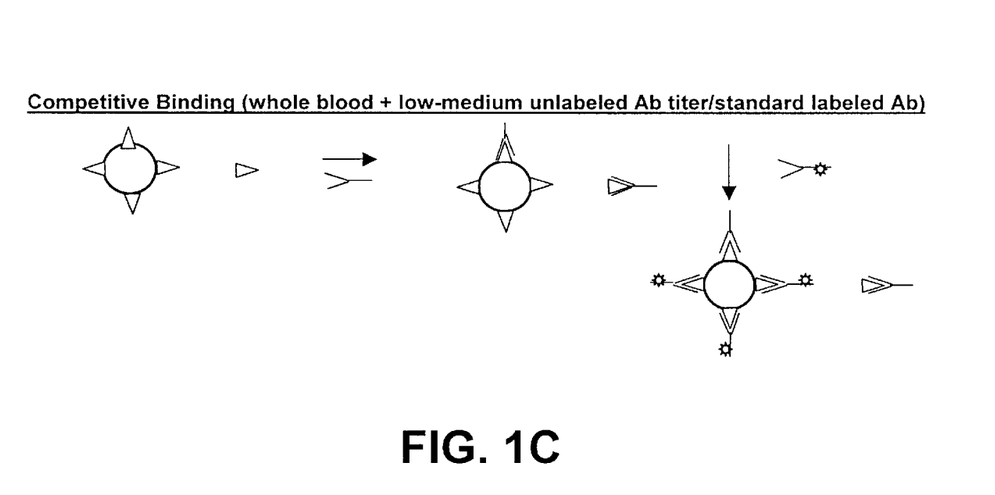
FIG. 1C is a schematic diagram showing competitive binding that occurs when the blood sample containing the cell-bound receptors and the soluble is contacted with a low to medium titer of unlabeled antibody and a standard titer of labeled antibody. In contrast to FIG. 1B, some of the unlabeled antibody binds the bound receptors as well as the unbound receptors.
Figure 1D:
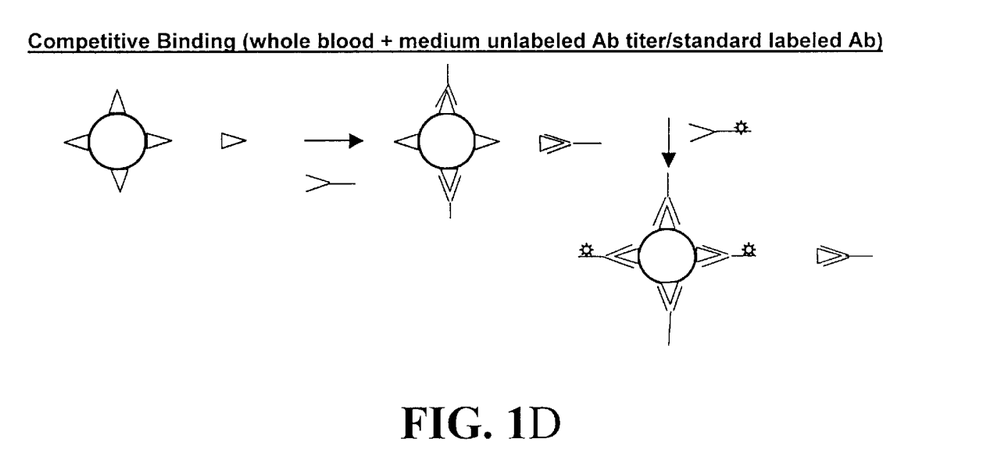
FIG. 1D is a schematic diagram showing competitive binding that occurs when the blood sample containing the cell-bound receptors and the soluble receptors is contacted with a medium titer of unlabeled antibody and a standard titer of labeled antibody.

A schematic diagram of the binding of labeled antibody to receptors on targeted cells and soluble receptors in the control is shown in FIG. 1A. Schematic diagrams of the binding of unlabeled and labeled antibody to receptors on targeted cells and soluble receptors in competitive binding samples is shown in FIGS. 1B through 1D.

According to another step of the method of this invention, each test sample from the competitive assay step as well as the control samples containing no unlabeled ligand are analyzed on an instrument that measures a signal using a parameter selected from the group consisting of direct current, radio frequency current, light scatter, fluorescence, and combinations thereof. The instrument detects only labeled ligands that are bound via the intact bound receptor on the surface of the formed body. The unlabeled ligand, soluble labeled ligand, and/or labeled ligand bound to soluble receptor are not measured. Most preferably, the instrument measures light scatter and fluorescent emission of formed bodies to which are attached receptor bound labeled ligands. For example, the excitation radiation from a flow cytometer causes the markers on the labeled ligands to produce a signal detectable as mean channel intensity of the fluorescence (or enhanced Raman intensity) or light scatter. Only the labeled ligands bound to receptors on the formed bodies are detected in this manner. The flow cytometer does not measure any unbound labeled ligand in the sample or any ligand bound to soluble receptors. Thus, for each set of control samples and test samples, mean channel intensity values for each concentration of labeled ligand in the control, and unlabeled and labeled ligand in the test sample, are obtained. The mean fluorescent intensities preferably span the range of receptor occupancy from about 1/100 to about 100% of saturation (saturation being defined as all receptor sites filled by labeled ligand).

According to another step of the method, a series of linear-log graphical dependence curves are plotted from the data gathered from the competition assay (test samples containing increasing concentrations of unlabeled ligand and a constant concentration of labeled ligand) and the control (containing increasing concentrations of labeled ligand only in a constant volume of sample). See, e.g., FIGS. 2 and 3 for examples of these curves. A first linear-log graphical dependence curve is formed by plotting the mean channel intensity values obtained from the competitive assay step against the known molar concentrations of the unlabeled ligand in the test samples (in FIG. 3; and in FIG. 2). A second linear-log graphical dependence curve is formed by plotting the mean channel intensity values against the known molar concentrations of the labeled ligand in the control samples (e.g., in FIG. 3; X in FIG. 2). A third linear-log graphical dependence curve is formed by plotting the mean channel intensity values against the molar concentrations of the known concentrations of the total labeled and unlabeled ligand in the test samples (in both FIGS. 2 and 3). Preferably, these curves are overlaid on a single graph for further analysis.

The method of this invention employs two of these graphical analyses to determine the concentration of soluble receptors released from the formed bodies into solution. A first molar concentration is identified that corresponds with the intersection of the second curve plotted using the concentrations of total labeled ligand only in the control (e.g., in FIG. 3; X in FIG. 2) with the third curve plotted using the concentrations of total ligand (labeled and unlabeled) in the test samples (in both FIGS. 2 and 3). The constant labeled ligand concentration in the competitive binding run (third curve) is then subtracted from the molar concentration of labeled and unlabeled ligand at the intersection of the two curves. The difference (D) provides the unlabeled ligand concentration that was bound to soluble receptor. The amount of soluble receptor is thereafter calculated by correcting the value of (D) for the binding stoichiometry between ligand and soluble receptor. The difference (D) is multiplied by the valence (e.g., number of binding sites) of the ligand, and the resulting value is the concentration of soluble receptor. Example 5 describes the performance of this method and these calculations in detail.

Such valences are known for immunoglobulins and their receptors. For example, where the ligand is an IgG antibody, the valence is 2. Where the ligand is the pentameric IgM antibody, the valence is 10. Where the ligand is other than an antibody, e.g., a hormone, a drug, etc., the number of sites on the ligand that can bind to the selected receptor can be determined by known methods. See, e.g., the methods described in U.S. Pat. No. 5,814,468, among others.

If this method is computer-implemented, the computer program may perform all of the above calculations and generate the intersection value without actually reproducing the curves referred to above. One of skill of the art would understand that this invention encompasses a method that can be performed without actual physical generation of the curves and plots. Such calculations required by the method can be performed by a computer program.

This method of the present invention has a number of advantages over other methods of the prior art, including that it provides significant additional accuracy to the method described in U.S. Pat. No. 5,814,468. Other advantages of this flow cytometric assay method for quantification of soluble analyte or soluble and bound analyte include the absence of any need for pure or partially pure antigen (where the analyte is a receptor on a pre-existing formed body, such as a biological cell) and the absence of any requirement for an extraneous solid support for any component of the reaction. For example, the present invention permits the modification of a known antibody competition immunoassay and an antibody capture immunoassay, both previously described in Harlow, E. and Lane, D., *Antibodies—A Laboratory Manual.* Cold Spring Harbor, N.Y.: Cold Spring Harbor Laboratory Press (1988) chap 14, p iii–ix and 553–569]. According to this invention, the assays are conducted without the presence of pure or partially pure antigen and without an extraneous solid support, such as microtiter plates or beads, for any component of the reaction when the analyte is a receptor on biological cells or other naturally-occurring formed bodies, and the receptor is also shed from these formed bodies. The elimination of these requirements, which are recommended for quantifying antigen in competition assays, allows the flow cytometric assay of this invention to be more easily performed in these samples which contain pre-existing formed bodies and receptors.

According to the following exemplified embodiments of the present invention, the cells in whole blood serve as the solid support for the assay. The above-described competitive binding protocol of unlabeled and labeled antibody for the same antigen in solution and on the surface of cells is thereby provided with flow cytometry as a sensitive technique to determine the concentration of soluble antigen in blood plasma. This method also allows determination of the specific avidity constant for binding of unmarked antibody to its antigen on a cell surface once the specific avidity constant of marked antibody was determined by other means, such as by the method described previously [Siiman, O. and Burshteyn, A., *Cytometry,* 40: 316–326 (2000); U.S. Pat. No. 5,814,468], and the number of antigenic receptors per targeted cell. The results of the method of this invention may also be used to correct cell surface antigen-antibody binding constants and receptor populations for the presence of the same antigen as a soluble component of blood plasma.

In the examples provided below, the method of this invention is employed for analysis of soluble and neutrophil-bound CD16b antigen. However, as stated above, this method may be used for quantification of many other soluble and cell bound receptors, e.g., the CD100 receptor shed in the context of spinal cord injury [C. Herold et al, *Leukocyte Typing* V, 288–292 (1995); S. Delaire et al, *Cell. Mol. Life Sci.,* 54:1265–1276 (1998)]. The method of this invention may also be used to determine only soluble analytes, such as for thyroid factor T4 or soluble prostate surface antigen, among many others. Similarly, this method may be employed to distinguish between the normal and diseased form of the prion protein, using plasminogen-coated beads, since plasminogen has been found to be the first factor that discriminates between normal and pathological prion protein [See, e.g., M. B. Fischer et al, *Nature,* 408:479–483 (2000)].

The methods of this invention are also useful for the quantification of non-biological analytes, e.g., for particular analytes in water or other fluids in which proteins are soluble. The method of this invention is both simple and inexpensive, requiring only a supply of purified unlabeled ligand (e.g., antibody) and suitable fluorescent labeled ligand (e.g., labeled antibody) against the same analyte (e.g., antigenic receptor), which occur both on the surface of the formed body (e.g., targeted cells) and in the sample (e.g., plasma in the blood serum).

In one embodiment this invention provides a method of diagnosing a disease characterized by an altered level of receptors shed by targeted cells into the blood of a mammal. The diagnostic method is performed by analyzing the amount of soluble receptor (e.g., CD100) shed from the surface of certain target cells (e.g., white blood cells) into blood samples of a mammal, preferably a human, suspected of having a disease, e.g., spinal cord damage. The analysis comprises the steps of performing a competition assay by incubating blood samples from this mammal containing a predetermined amount of the targeted WBC, with a constant known concentration of an antibody, (e.g., anti-CD100 that binds to a known receptor CD100 on WBC in cord blood) labeled with a detectable marker (e.g., FITC), and with varying known concentrations of unlabeled antibody. The labeled antibody and the unlabeled antibody compete for binding to both the WBC-bound and soluble CD100 receptors. Each sample from the first step and a control sample containing the same predetermined amount of WBC and varying known concentrations of the labeled antibody with no unlabeled antibody are irradiated with excitation radiation. The radiation causes the FITC markers on the labeled antibodies bound to the WBC-bound CD100 receptors to produce a signal detectable as mean channel intensity values of fluorescence or light scatter.

A first linear-log graphical dependence curve is formed by plotting the mean channel intensity values against the molar concentration of the unlabeled antibody in the test samples. A second linear-log graphical dependence curve is formed by plotting the mean channel intensity values against the molar concentration of the labeled antibody in the control samples, and a third linear-log graphical dependence curve is formed by plotting the mean channel intensity values against the molar concentration of total labeled and unlabeled antibody in the test samples.

The concentration of soluble receptors released (shed) from the WBC in the patient's blood sample into solution is determined by evaluating the difference between the molar concentration that corresponds with the intersection of the second curve and the third curve and the constant labeled antibody concentration used in the test samples to construct the third curve, followed by applying the binding stoichiometry between the antibody and antigenic receptor.

Thereafter, the resulting concentration of soluble CD100 receptors from the mammal's blood samples is compared with known normal concentrations of soluble CD100 receptors in blood samples containing the same predetermined number of WBC from healthy mammals. A significant difference between the concentration of the soluble CD100 receptors in the mammal's blood sample and the normal concentrations is indicative of disease, e.g., in this case, of serious spinal cord injury.

It is clear from this disclosure that one of skill in the art may employ the above-defined method for the diagnosis or treatment monitoring of other diseases characterized by shedding of bound receptors from target cells, e.g., blood cells, or other diseases in which the receptors or analytes are not naturally bound but are soluble. In the latter case, the formed bodies containing bound analyte would be synthetically prepared, e.g., polystyrene beads to which the analytes were covalently linked.

Further advantages of this invention may be seen in a comparison of the time required for completion of, and costs of reagents required in, the competitive antibody binding assay using flow cytometry of this invention with those issues in conventional enzyme linked immunosorbent assay (ELISA) and radioimmunoassay (RIA) methods. Firstly, ELISA and RIA usually require overnight incubation of capture antibody with the solid surface, either plates or beads. The method of the present invention involving flow cytometric analysis does not need lengthy incubation times or precautions regarding the use and disposal of radioactive material. Secondly, ELISA as well as RIA needs work-up times of 3–4 hours for sample incubation, peroxidase second antibody incubation, substrate incubation, washes, and measurement of serially diluted samples and standards. In contrast, the assay of the present invention requires about 10 minutes as an incubation time of labeled antibody (labeled ligand) with cell samples for semi-quantitative results. In the examples provided below, two 1 hour incubation periods for mixing titers of unlabeled ligand and, then, labeled ligand (e.g. antibody) with cells were used for quantitative assay results, followed by measurements on the flow cytometer to give a total analysis time of about 2.5 to 3 hours. This represents a considerable time savings in the present flow cytometric assay over an ELISA or RIA.

The ELISA and RIA methods require more different types of antibody reagents, albeit in smaller quantities, than the flow cytometric assay of the present invention. Also, ELISA assays require a control with known amounts of antigen or other analyte. Such a control may be difficult to obtain and characterize for the first time, making the expense and effort involved in preparing and purifying a suitable control enormous.

C. Other Embodiments of the Invention

1. Kits

In yet another aspect of this invention, a kit is provided for performance of the method of this invention. Preferably such kits are employed for performing the diagnostic methods of this invention. However, similar kits may be assembled where the methods of the invention are to be employed to identify and quantify industrial or commercial analytes, e.g., contaminants or markers in liquids, etc. The components of this method are readily adaptable into a kit that contains one or more ligands, both labeled and unlabeled or one or more detectable markers for labeling a suitable ligand, synthetic formed bodies, e.g., polystyrene beads, reagents suitable for covalently linked analyte to the beads, suitable vessels for containing samples, and suitable controls or tables of normal values of soluble analyte, e.g., shed or soluble receptors. The kit of the present invention can contain either the same or different detector markers, whereby a plurality of samples can be examined with the same detectors or with multiple detectors. These kits can additionally contain reagents necessary to maintain or preserve the samples. More importantly, the kit contains instructions for performing the competitive assay and preparing the controls. Also provided in a kit may be suitable diluents and buffers for the samples, indicator charts for signal comparisons, disposable gloves, decontamination instructions, applicator sticks or containers, and sample preparator cups. The kits preferably also contain necessary buffer substances or media, as required. One of skill in the art could assemble any number of kits with the information and components necessary to perform the method on a patient for any specific receptor and target cell, and compare the results to norms for that receptor.

2. Computer-Implemented Methods

In still another embodiment and advantage of the method of this invention, the above-described methods are implemented by one or more computer programs. A computer program is provided that performs the analysis and calculations described above. This program generates the linear-log graphical dependence curves described above. More specifically, the computer program is designed to record, sort and calculate the parameters of the method provided above, including the mean channel values, the molar concentrations of the ligands, the identification of the intersections and to obtain the necessary analytical results. In a preferred embodiment, this computer program is integrated into the particle analysis instrument, particularly a hematology instrument or flow-cytometer. In still other embodiments, the program is on a separate computer, which is a "plug-in" device for attachment to the analysis instrument. Still another embodiment of this invention is a computer program that is present on a standalone computer, into which data from the instrument is fed. Alternatively, the method of this invention can be generated by use of conventional spreadsheet programs on standalone personal computers.

This computer program comprises means for translating electrical pulse data recorded as a range of mean channel fluorescence intensity numbers and concentrations or titers of ligand populations in samples into overlapping plots of mean fluorescence intensity vs molar concentrations of unlabeled ligand in a test samples, labeled ligand in a control sample and total ligand in a test sample. A graphical analysis of the three overlapping curves is produced by use of this data. This program also comprises a means for analyzing these curves to obtain the point of intersection, and further to calculate the concentration of soluble analyte in the samples. Thus, the program preferably performs all of the calculations necessary to perform the method of this invention by analyzing the data on the test or control samples of containing formed bodies, and/or soluble analytes and bound analytes. In still another embodiment of this program, it can provide an electrical signal or warning when an aberrant result is identified.

In still another embodiment of this invention, an analysis instrument, e.g., a flow cytometer, is provided that comprises an integrated computer program which identifies and analyzes the amount of soluble analyte in a sample, e.g., soluble receptor shed from the surface of a formed body into solution in a sample comprising formed bodies by implementing the program and method steps described above.

D. Examples of This Invention

The following examples demonstrate the methods of the present invention, and demonstrate its use in analyzing and enumerating the highly variable expression of the 1D3 or 3G8, which are Fcγ RIIIB antigenic receptors on neutrophils in normal blood donors. The following examples illustrate various aspects of this invention. These examples do not limit the scope of this invention, which is defined by the appended claims.

Example 1

Monoclonal Antibodies

All of the monoclonal antibodies referred to herein are identifying designations used by Beckman Coulter, Inc. for monoclonal antibodies made by Coulter. The term "CD" refers to "Cluster Designation" adopted by the International Workshops on Human Leukocyte Differentiation Antigens. The American Type Culture Collection, located at 10801 University Boulevard, Manassas, Va. 20110–2209 is identified by the abbreviation ATCC.

An antibody specific to neutrophils, 1D3 (anti-CD16b or anti-Fcγ RIIIB) is an IgM monoclonal. The 1D3 clone [ATCC Deposit No. HB 9445] was derived from fusion of Balb C mouse spleen cells immunized with purified human granulocytes and NS-1 plasmacytoma mouse myeloma cells [U.S. Pat. No. 4,931,395]. In attempting to use 1D3-conjugated magnetic beads [U.S. Pat. Nos. 5,466,609 and 5,707,877] to specifically deplete neutrophils from whole blood samples so that any remaining granulocytes (basophils and eosinophils) could be enumerated more precisely from COULTER® VCS™ (Volume-Conductivity-Scatter) plots [U.S. Pat. No. 5,262,302], the inventors discovered that many normal blood donors did not allow complete depletion of neutrophils. The reagents 1D3 (IgM) and fluorescein isothiocyanate-labeled 1D3 (1D3-FITC) are commercially available from Beckman Coulter, Inc.

3G8 is an anti-CD16b, IgG1 monoclonal antibody. The 3G8 receptor is expressed on neutrophils, most (90%) natural killer cells, macrophages, and a subpopulation (10%) of peripheral blood monocytes. It cannot be detected on peripheral blood B and T cells of most individuals. More recent literature [Teillaud, J. L., et al, Immunomethods, 4: 48–64 (1994); Galon, J. et al, J. Immunol., 157: 1184–1192 1996); Kindzelskii, A. L. et al, J. Immunol., 164: 953–958 (2000); Van Eeden, S. F. et al, J. Immunol. Meth., 232: 23–43 (1999); Kuijpers, T. W. et al, J. Immunol. Meth., 232: 211–229 (1999)] has revealed that the investigation of soluble Fcγ RIIIB as well as its complexes with other serum components such as IgG and complement has become a more active area. The reagents 3G8 (IgG1) and fluorescein isothiocyanate-labeled 3G8 (3G8-FITC) are commercially available from Beckman Coulter, Inc.

CD45 antibody was derived from hybridization of mouse Sp2/0-AG14 myeloma cells with spleen cells from BALB/c mice immunized with a derivative of the CEM cell line.

Other reagents used herein and commercially available from Beckman Coulter, Inc. are: MsIgG1-RD1/MsIgG1-FITC: Mouse IgG1-phycoerythrin (RD1)/Mouse IgG1-FITC; and CD45-RD1.

Example 2

Preparation of Beads

1D3-DAP-PS magnetite beads that were used in magnetic bead depletions were prepared according to the methods described for the preparation of 1D3-aminodextran-PS magnetite beads [see, e.g., U.S. Pat. Nos. 5,466,609; 5,707,877; 5,639,620 and 5,776,706, incorporated by reference herein]. However, 1,3-diaminopropane (DAP), in place of aminodextran, was first coupled to the bead surface. Conjugation of the 1D3 monoclonal antibody to phycoerythrin (RD1) was accomplished by reacting sulfo-SMCC (sulfosuccinimidyl 4-[N-maleimidomethyl] cyclohexane-1-carboxylate) -activated 1D3 antibody with IT (2-iminothiolane) -activated RD 1.

Example 3

Flow Cytometric Measurements

The COULTER® Profile II™ or COULTER® EPICS® XL-MCL™ flow cytometer was used as described in Siiman, O. and Burshteyn, A., Cytometry, 40: 316–326 (2000), incorporated herein by reference. CD16b+ cells were analyzed with appropriate fluorescent markers by gating on the granulocyte population in the forward versus side light scattering histogram.

Example 4

Depletion Characteristics of Neutrophils from Whole Blood with 1D3-Magnetic Beads Neutrophils in whole blood of normal donors which show bright mean channel fluorescence intensity (MFI>12) when labeled with markers such as 1D3-FITC and analyzed by flow cytometry have been previously shown to be easily depletable with 1D3 antibody-conjugated magnetic beads [U.S. Pat. Nos. 5,466,609 and 5,707,877]. However, many normal blood donors, that showed dim (MFI<6) or medium (6<MFI <12) brightness in mean channel fluorescence intensity of neutrophils labeled with 1D3-FITC or 1D3-RD1, were undepletable. They showed more than 1–2% neutrophils remaining after depletion with 1D3-conjugated magnetic beads. A 1–2% difference was typically observed between flow cytometric data and COULTER STKS hematology instrument data for % neutrophils due to the presence of 1–2% immature neutrophils. These immature neutrophils lack the expression of certain antigens such as 1D3(CD16b) on the cell surface. The following examples of bright, medium, and dim donors were typical.

In the experiments described below, test samples were prepared by mixing 200 $\mu$L of whole blood in 10×75 mm$^2$ glass tubes with varying titers of a labeled ligand, i.e., 2.5% w/v 1D3-DAP-PS magnetite beads (41% magnetite, 0.7 $\mu$m diameter) in volumes from 40 to 2.5 $\mu$L. In each successive test sample, the titer of the labeled ligand was decreased by a factor of ½. The control sample contained no beads. The total volume of each test sample and the control sample was adjusted to 240 $\mu$L with 1×PBS buffer solution before mixing. Mixing time in a multitube vortexer was 2 minutes, followed by magnetic separation for at least 2 minutes. Thereafter, supernatant samples for each test sample were carefully pipetted from the tubes to avoid disturbing the separated residue The undepleted control sample and various depleted test samples were then mixed with 20 $\mu$L of dual labeled ligand, 0.4 $\mu$g/$\mu$L 1D3-FITC/0.5 $\mu$g/$\mu$L CD45-RD1, for 10 minutes and run on the COULTER® TQ-Prep™ instrument to lyse red blood cells and quench the reaction. These samples were then run on the flow cytometer to determine the mean channel fluorescence intensity (MFIs) of the labeled antibody 1D3-FITC gated on granulocytes and the percentage neutrophils in the white blood cell population.

A series of experiments was performed using samples from five random donors from a normal blood donor pool. The samples were undepleted and depleted with 40 $\mu$L of beads. The MFIs (standard deviations in parentheses) and % neutrophils in the white blood cell population were reported in Table 2:

TABLE 2

| Samples | Donor | MFI | Std Dev'n | % neutrophils |
|---|---|---|---|---|
| Undepleted | 1 | 10.36 | (4.23 | 36.8 |
| | 2 | 9.42 | (3.44) | 47.7 |
| | 3 | 1.66 | 0.68 | 31.2[a] |
| | 4 | 16.45 | (4.92) | 68.5 |
| | 5 | 4.83 | (2.46) | 49.5 |
| Depleted | 1 | 7.96 | (3.24) | 18.4 |
| | 2 | 0 | | 0.6 |
| | 3 | 1.69 | (0.73) | 36.3[b] |
| | 4 | 0 | | 1.1 |
| | 5 | 4.50 | (2.17) | 43.1 |

[a]gate error, below discrimination line
[b]gate error

The brightest donor #4 gave data for % neutrophils in samples depleted with 1:1, 1:2, 1:4, 1:8, and 1:16 dilution of beads as follows: 1.1, 4.2, 4.6, 5.1, and 5.4. This level of depletion even at the 1:16 dilution of beads (2.5 $\mu$L of 2.5% w/v solids beads+37.5 $\mu$L 1×PBS buffer solution+200 $\mu$L of whole blood) could not be achieved with donors, #5 and #3, at the 1:1 dilution of beads because of the presence of large amounts of soluble CD16b antigen in the serum of the blood samples.

For another series of experiments, in run 1 for EDTA-anti-coagulated whole blood, the MFIs and % neutrophils for the 0 to 40 $\mu$L bead titers were reported in Table 3. Similar data for run 2, in which a sample of whole blood from the same donor was centrifuged for 5 minutes at 500 g, the supernatant plasma was removed and replaced with an equal volume of 1×PBS buffer solution, and then mixed, gave the following data in Table 3. The washed sample was 95% depleted of neutrophils with 40 $\mu$L of 2.5% w/v magnetic beads, whereas the unwashed sample was only 53% depleted of neutrophils at the same titer.

TABLE 3

| Run | Donor | MFI | Std Dev'n | % neutrophils |
|---|---|---|---|---|
| 1 | 1 | 5.452 | (3.323) | 59.6 |
| | 2 | 3.037 | (1.616) | 49.3 |
| | 3 | 2.774 | (1.420) | 48.2 |
| | 4 | 2.632 | (1.314) | 40.7 |
| | 5 | 2.350 | (1.135) | 40.8 |
| | 6 | 1.936 | (0.883) | 28.1 |
| 2 | 1 | 4.149 | (2.600) | 59.1 |
| | 2 | 3.204 | (1.974) | 29.4 |
| | 3 | 2.901 | (1.820) | 25.5 |
| | 4 | 2.416 | (1.444) | 19.3 |
| | 5 | 1.804 | (0.891) | 9.6 |
| | 6 | 1.503 | (0.692) | 3.0 |

From characteristics of the above magnetic beads (density of 1.569 g/cm$^3$ and diameter of 0.70 $\mu$m) and the whole blood sample (9.0×10$^5$ WBC/100 $\mu$L of blood as determined on the COULTER® S-Plus™ counter) an estimate of the minimum number of receptors/cell needed to be occupied by magnetic beads to enable depletion of neutrophils by magnetic separation can be made.

Thus, the 40 $\mu$L of 2.5% w/v solids beads contains a total volume of 6.410×10$^{-4}$ cm$^3$ of solids beads. The volume per spherical bead is calculated as 1.796×10$^{-13}$ cm$^3$, which gives a total of 3.569×10$^9$ beads in the titer of beads. If each bead corresponds to a single occupied receptor site on the cells, then there are a minimum of 3.569×10$^9$ 1D3 receptor sites in the sample of whole blood that was depleted.

With 59.1 % neutrophils in the white blood cell population of the donor, a 200 $\mu$L whole blood sample taken for depletion, and 5.3×10$^5$ neutrophils per 100 $\mu$L of blood, there were a total of 1.06×10$^6$ neutrophils in the sample that was depleted. Therefor, the minimum average receptor/neutrophil ratio that allowed magnetic depletion of the neutrophils was 3.3×10$^3$.

Also 0.46×10$^6$ neutrophils were left undepleted in the unwashed sample, representing 1.485×10$^9$ beads associated with shed antigen. With an area per IgM molecule on the magnetic bead (700 nm dia.) surface of about 256 nm$^2$ (four times that of an IgG antibody), the maximum number of IgM per bead is 6010. With this latter value and a reduced valence of 2 for surface bound IgM, there are at most 8.9×10$^{16}$ receptors per L or 150 nM shed receptors for 200 $\mu$L of whole blood.

This example demonstrates the ability to magnetically deplete the washed blood sample but not the unwashed whole blood of targeted neutrophils. These data support several conclusions. First, 1D3 receptors on neutrophils were not blocked by, for example, antibody in circulation. Second, binding of fluorescently labeled ligand to antigenic sites on neutrophils did not cause receptors to be capped into islands on the neutrophil surface so that quenching of marker fluorescence was observed. However, shed (i.e., soluble) receptors in the blood plasma preferably occupied 1D3 antibody sites on the magnetic beads because of their much higher kinetic energy and thus diffusion constant compared to receptors on the surface of neutrophils, which have average diameters of 10–15 μm.

Moreover, the targeted neutrophils were able to replenish 1D3 antigen on the cell surface that had been shed into the blood plasma, by some mechanism such as translocation [Huizinga T. W. J. et al, *J. Clin. Invest.*, 86: 416–423 (1990)] from preformed subcellular pools of receptors present on intracellular stores so that neutrophils were depletable by magnetic bead separation.

Example 5

Competitive Antibody Binding to Soluble Antigen and Antigen on Biological Cells by Flow Cytometry—the Cytoimmunoassay (CYIA)

The following protocol is applicable when the concentration of unlabeled ligand (antibody) is varied and the concentration of labeled ligand (labeled antibody) is kept constant. The concentration of labeled antibody in the control is chosen so that about 80–90% of saturation of receptor sites on targeted cells is obtained. See, e.g., FIG. 1A. The binding of unlabeled and labeled antibody to receptors on targeted cells and soluble receptors in competitive binding samples is shown in FIGS. 1B through 1D.

A. Experiment 1

10 μL of variable amounts (1/100 to 100 times the standard amount of 4 μg) of unlabeled 1D3 antibody were first incubated for one hour with whole blood samples (100 μL). Thereafter, for an additional one hour, all samples were incubated with the standard 10 μL of dual fluorescent labeled antibody (ligand) 1D3-FITC/CD45-RD1. The total concentration of labeled ligand 1D3-FITC in each sample before TQ-Prep™ was $3.92 \times 10^{-8}$ M. All samples were then run on the TQ-Prep™ and analyzed on the flow cytometer.

Figure 2:
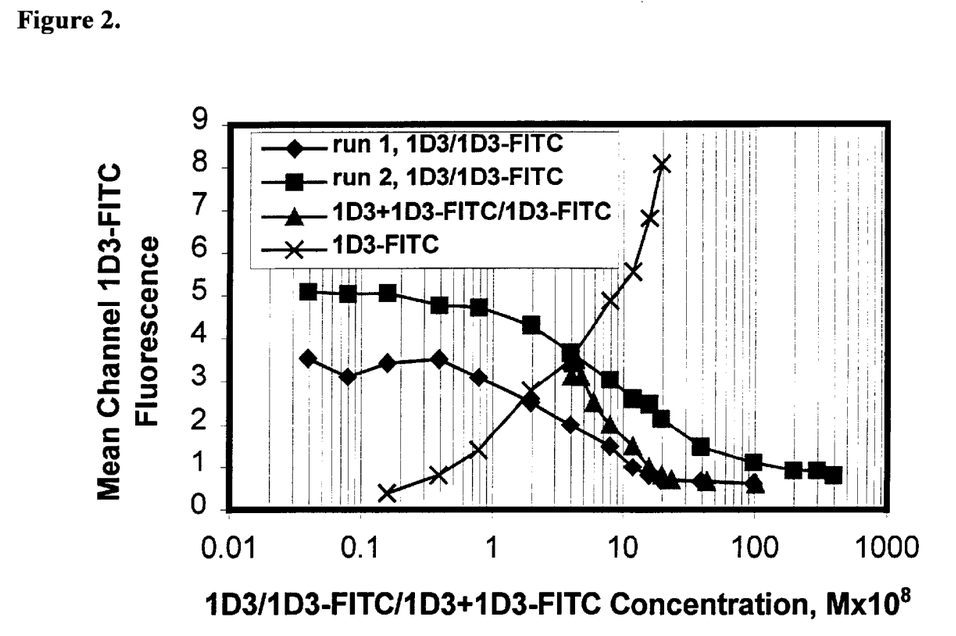

The mean channel 1D3-FITC fluorescence intensity thus recorded was plotted in FIG. 2 against the concentration in mol/L of unlabeled 1D3 antibody that was used per sample. A small rise in MFI was observed in the competitive assay run 1 (MFI=2.8) and run 2 (MFI=4.9) compared to the control that contained no unlabeled antibody. Thereafter, a fall in fluorescence intensity was noted at the lowest titers in the plot. This small rise in MFI indicated the reaction of soluble antigen with unlabeled antibody, which increased the intensity of fluorescent labeled antibody on cell-bound antigen. Without the competition of the unlabeled antibody on the soluble antigens, the labeled antibody might otherwise have bound to soluble antigen and would not be detected by flow cytometry. The step-by-step progress to obtain this initial rise and fall of labeled antibody fluorescence intensity on targeted cells is schematically shown in FIGS. 1A through 1D.

This sensitivity in fluorescence intensity on targeted cells due to the presence of soluble antigen could not be achieved in the reverse competitive antibody mode, i.e., variable concentration of labeled antibody and constant concentration of unlabeled antibody because of the very low fluorescence intensities at low variable titers at which binding occurs to soluble antigen. The latter phase in the graph (FIG. 2) is followed by a sigmoidal curve in which there is a smooth decrease in intensity as unlabeled antibody took up bound antigenic sites on the targeted cell surface in competition with labeled antibody. This decrease was log-linear over one to two decades of 1D3 antibody concentration.

Finally, a plateau was reached at a lower level where all sites were filled by unlabeled antibody and the intensity corresponded to the spontaneous fluorescence of the cells. The point at which the curve passes below the intensity of the control at low concentrations of unlabeled antibody 1D3 can be used to estimate the end-point in the titration of free soluble antigen in the blood sample. The intensity of the control is reached when enough unlabeled antibody 1D3 has been added to react with soluble antigen, so that the concentration of labeled antibody, 1D3-FITC, available to the targeted cells is the same as it was in the control.

A more precise analytical way of finding the end-point is to determine the total concentration of antibody (unlabeled+labeled) for a competitive binding run (test sample) and a labeled antibody only run (control sample) at which the labeled antibody fluorescence on targeted cells is the same. This was done in each run.

Table 4 shows the data for a dim donor in run 1 (single whole blood-1D3 antibody-dual labeled antibody sample per titer point) and for a second dim donor in run 2 (samples in triplicate per titer point). Also shown are the mean channel 1D3-FITC fluorescence intensities per aliquot of unlabeled antibody 1D3 added to 100 μL whole blood for runs 1 and 2. The mean channel 1D3-FITC fluorescence intensities per aliquot of 1D3-FITC added to 100 μL whole blood for run 1 are also indicated in Table 4. The values in parentheses are standard deviations.

TABLE 4

Mean channel 1D3-FITC fluorescence intensity

| μg 1D3 or 1D3-FITC | Run 1 1D3-FITC alone | Run 2 Trial 1 | Trial 2 | Trial 3 | Mean |
|---|---|---|---|---|---|
| .040 | 3.545 (1.802) |  | 4.924 (2.724) | 5.119 (2.955) | 5.206 (3.005) | 5.083 |
| .080 | 3.110 (1.627) |  | 5.084 (2.795) | 5.013 (2.777) | 5.028 (2.795) | 5.042 |
| .160 | 3.440 (2.250) | 0.4 | 5.066 (2.824) | 5.012 (2.713) | 5.089 (2.842) | 5.056 |
| .400 | 3.528 (2.426) | 0.8 | 4.910 (2.687) | 4.826 (2.654) | 4.553 (2.412) | 4.763 |
| .800 | 3.098 (1.723) | 1.4 | 4.660 (2.469) | 4.743 (2.670) | 4.727 (2.712) | 4.710 |
| 2.00 | 2.5 | 2.774 (1.251) | 4.258 (2.222) | 4.433 (2.345) | 4.211 (2.175) | 4.301 |
| 4.00 | 2.0 | 3.496 (1.751) | 3.141 (1.423) | 3.940 (2.021) | 3.925 (2.062) | 3.669 |
| 8.00 | 1.5 | 4.875 (2.635) | 3.051 (1.480) | 3.089 (1.445) | 3.008 (1.400) | 3.049 |
| 12.0 | 1.0 | 5.551 (3.229) | 2.476 (1.045) | 2.854 (1.357) | 2.456 (1.034) | 2.595 |
| 16.0 | 0.80 | 6.810 (3.933) | 2.502 (1.058) | 2.463 (1.063) | 2.446 (1.062) | 2.470 |
| 20.0 | 0.70 | 8.078 (4.808) | 2.1 | 2.2 | 2.1 | 2.13 |
| 40.0 | 0.65 |  | 1.5 | 1.5 | 1.4 | 1.47 |
| 100. | 0.60 |  | 1.1 | 1.3 | 1.0 | 1.1 |
| 200. | — |  | 0.90 | 0.90 | 0.90 | 0.90 |
| 300. | — |  | 0.90 | 0.90 | 0.90 | 0.90 |
| 400. | — |  | 0.80 | 0.80 | 0.80 | 0.80 |
| Control |  |  | 4.711 (2.602) | 4.974 (2.803) | 4.942 (2.742) | 4.876 |

The end-points for titration of soluble 1D3 antigen (Fcγ RIIIB) in runs 1 and 2, as read from the graphs in FIG. 2, are both at about 4 nM of 1D3 antibody (850,000 Daltons). The same end-point is also obtained from the intersection of the 1D3-FITC binding curve with the total antibody concentration (1D3+1D3-FITC) curve in competitive binding in FIG.

2, at a total antibody concentration of $4.3\times10^{-8}$M, or an unlabeled antibody concentration of $0.4\times10^{-8}$M.

Assuming an antigen valence of one and a 10:1 stoichiometry of antigen:IgM antibody in the region of antigen excess, this corresponds to a 4 nM×10×120 μL/100 μL=48 nM concentration of soluble 1D3 antigen in the serum of each dim donor. This figure falls in the middle of the range of soluble 3G8 antigen (also Fcγ RIIIB) in normal serum, which was determined by ELISA [Fleit H. B., et al, *Blood*, 79:2721–2728 (1992)] to be 7.3 to 75.9 nmol/L.

B. Experiment 2

Furthermore, a competitive binding experiment was also done by mixing 100 μL of whole blood with 10 μL titers (1/100 to 280×the standard amount of 0.75 μg) of 3G8 unlabeled antibody and 30 μL of 1×PBS buffer solution for one hour. Then, a fixed amount of dual labeled ligand, 0.75 μg 3G8-FITC/5.0 μg CD45-RD1 in a 10 μL titer, was added to the sample. The sample was then incubated for another hour, run on the TQ-Prep™, and analyzed on the flow cytometer. The total concentration of labeled ligand 3G8-FITC in each sample before TQ-Prep™ was $3.08\times10^{-8}$M. The results, shown as a log-linear plot in FIG. 3 of labeled ligand 3G8-FITC mean channel fluorescence intensity versus total concentration of unlabeled 3G8 antibody, gave a wide region from $3.08\times10^{-10}$ to $5.4\times10^{-8}$M of unlabeled 3G8 antibody in which the intensity (MFI=37–32) of labeled antibody 3G8-FITC was greater than in the control (MFI= 32) without any unlabeled 3G8 antibody.

Figure 3:
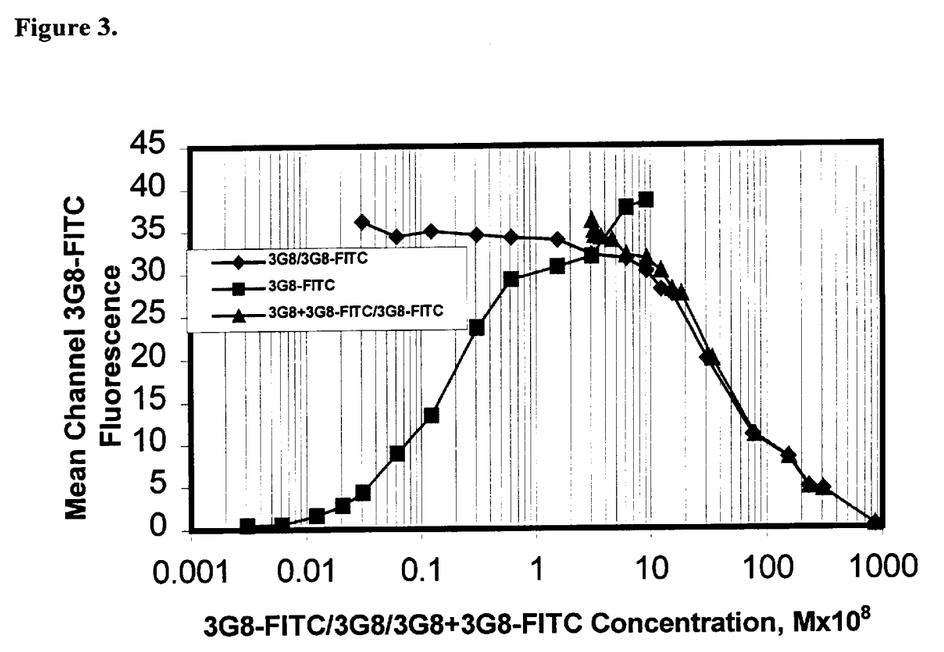
FIG. 3 is a linear-log graphical dependence of mean channel fluorescence intensity of labeled antibody (3G8-FITC) vs (◊) the molar concentration of unlabeled antibody (3G8) in a competitive binding run (test sample), (□) the molar concentration of labeled antibody 3G8-FITC in a non-competitive binding run (control), and (▲) the molar concentration of total antibody (3G8+3G8-FITC) in the competitive binding run (test sample).

Initially, the endpoint for titration of soluble 3G8 antigen was estimated at the point where the curve drops to the mean channel intensity of the control, i.e., $5.4\times10^{-8}$M unlabeled 3G8 antibody. More accurate quantification was achieved by evaluating the intersection of two binding curves of concentration versus mean channel fluorescence intensity of 3G8-FITC: (a) labeled antibody 3G8-FITC alone; (b) total unlabeled and labeled antibody, 3G8+3G8-FITC, in the 3G8/3G8-FITC competitive binding (test sample) as shown in FIG. 3. The intersection represents the same 3G8-FITC fluorescence intensity at a total antibody concentration of $3.8\times10^{-8}$M, or unlabeled 3G8 concentration of $0.7\times10^{-8}$M.

Assuming an antigen valence of one and a 1:2 binding stoichiometry between 3G8 (IgG1) antibody and soluble CD16b antigen in the region of antigen excess, the concentration of soluble 3G8 antigen for this blood donor is determined to be about 7 nM×2×150 μL/100 μL=21 nM.

C. Conclusions

Donors may show medium 1D3 marker fluorescence intensity at saturation of sites on neutrophils but show a large amount of soluble 1D3 receptor as indicated by low fluorescence intensity at beginning of titration of whole blood sample with labeled ligand. Higher fluorescence intensity was noted at the beginning of titration in competitive binding runs than the fluorescence intensity of the control without any unlabeled antibody.

The shedding of Fcγ RIIIB receptors from neutrophils to give high concentrations of soluble antigen does not necessarily deplete all receptors from the affected cells. Rather, translocation of receptors from subcellular pools to the surface of the cell has been invoked as a mechanism to account for the observed high surface receptor density despite observation of high concentrations of shed receptors [see, e.g., Huizinga T. W. J. et al, *J. Clin. Invest.*, 86: 416–423 (1990)].

Other unlabeled and labeled antibodies of KC48 (anti-CD15), which labels all granulocytes including neutrophils, were previously used to make a comparison with the binding equilibria of unlabeled 1D3 and labeled 1D3-FITC and of unlabeled 3G8 and labeled 3G8-FITC with CD16b antigen in whole blood. This was done to verify the competitive binding characteristics of monoclonal antibodies that bind antigens not normally shed in whole blood. The results, as described in U.S. Pat. No. 5,814,468, for unlabeled KC48 and labeled KC48-FITC competitive binding to antigen in whole blood, showed no initial rise in intensity to a maximum above the intensity of the control at low titers of unlabeled KC48 antibody. A standard sigmoidal curve was obtained in the plot of KC48-FITC fluorescence intensity versus total concentration of unlabeled KC48 antibody.

The equilibrium constants for binding of unlabeled antibody 1D3 or 3G8 to their antigenic sites on targeted neutrophils [U.S. Pat. No. 5,814,468] are very similar to the equilibrium constants for binding of labeled antibody, 1D3-FITC or 3G8-FITC, to the same antigenic site. Thus, the method used in the cytometric immunoassay for soluble CD16b antigen is useful quantitatively.

Magnetic bead depletion of neutrophils in whole blood with CD16b antibody-conjugated beads, as measured by flow cytometric analysis of the remaining cell suspension, was inhibited by the presence of soluble CD16b antigen in the blood plasma of normal donors. Normal blood donors showed serum concentration levels of shed CD16b antigen in the range of 1 to 50 nM as determined by a flow cytometric competitive binding assay. These figures compared favorably with parallel determinations using magnetic bead depletion of targeted neutrophils, for washed and unwashed whole blood samples to evaluate the concentration of shed CD16b antigen.

All documents cited above are incorporated by reference herein. Numerous modifications and variations of the present invention are included in the above-identified specification and are expected to be obvious to one of skill in the art. Such modifications and alterations to the compositions and processes of the present invention are encompassed in the scope of the claims appended hereto.

What is claimed is:

1. A method of analyzing the concentration or amount of a soluble first analyte in a sample, the method comprising the steps of:
   (a) providing said sample containing formed bodies to which are bound multiple said first analytes in bound form, and said first analytes shed from said formed bodies and present in said sample in soluble form;
   (b) providing from said sample a plurality of incubated test samples, wherein a first test sample contains:
      i. an unknown concentration of said soluble first analyte,
      ii. a predetermined amount of said formed bodies,
      iii. a known concentrations of an unlabeled first ligand that binds to said first analyte in either its bound or soluble form, and
      iv. a known concentration of a first ligand labeled with a detectable marker that produces a signal,
      wherein said labeled first ligand and said unlabeled first ligand compete for binding to said first bound analytes and said first soluble analytes, and
      wherein each second and additional said test sample differs from said first test sample and every other additional test sample by containing a different known concentration of said unlabeled first ligand;
   (c) providing a plurality of incubated controls, wherein a first control contains:
      i. the same predetermined amount of said formed bodies as present in said test samples of (b); and
      ii. a known concentration of said labeled first ligand with no unlabeled first ligand, wherein each second and additional control differs from said first control and every other additional control by containing a different known concentration of said labeled first ligand; and wherein after incubation of each control, said formed bodies in each control are between 1% and 100% coated with labeled first ligand bound to said bound first analyte;

(d) analyzing each said test samples (b) and each said control (c) individually in an instrument that measures a detectable signal being produced in each test sample or control only from complexes formed by said labeled first ligands bound to said bound first analytes;

(e) plotting a first curve from said signals measured from each of said plurality of controls against the known concentration of said labeled first ligand in each of said controls, and plotting a second curve from said signals measured from each of said plurality of said test samples against the known concentration of total labeled and unlabeled first ligand in each of said test samples;

(f) identifying the intersection of said first curve and said second curve;

(g) determining the concentration of unlabeled first ligand that bound to soluble first analytes in each said test sample (b) by evaluating the difference D between the concentration that corresponds with said intersection and the known labeled first ligand concentration in each said test sample (b); and (h) determining the concentration of said soluble first analytes in each said test sample (b) by determining the product of the value D and the binding stoichiometry of said labeled and unlabeled first ligand to said first analyte in soluble form.

2. The method according to claim 1, wherein said test sample and controls are purified of any particles that are not first analytes.

3. The method according to claim 1, wherein said formed bodies are particles to which said first analytes are covalently bound, said bodies either naturally occurring or synthetic.

4. The method according to claim 3, wherein said formed bodies are selected from the group consisting of synthetic polymeric beads, aminodextran-coated polystyrene beads, colloidal particles that have analytes covalently bound to their surfaces, biological cells, bacteria, viruses, and parasites.

5. The method according to claim 4, wherein said formed bodies are mammalian blood cells.

6. The method according to claim 5, wherein said formed bodies are white blood cells.

7. The method according to claim 1, wherein said first analyte is a proteinaceous or chemical composition which is naturally or synthetically covalently bound to a formed body or can exist in soluble form.

8. The method according to claim 7, wherein said first analyte is a cell-surface receptor either bound to said cell or shed therefrom.

9. The method according to claim 8, wherein said receptor is an antigenic receptor either bound to a white blood cell or shed therefrom.

10. The method according to claim 9, wherein said receptor when bound is linked to said white blood cell via a glycosyl-phosphatidylinositol linkage.

11. The method according to claim 1, wherein said first ligand is selected from the group consisting of a monoclonal antibody or recombinant antibody of classes IgG, IgM, IgA, IgD and IgE, a Fab, Fab' or F(ab')2, or Fc antibody fragment thereof, a single chain Fv antibody fragment, a recombinant construct comprising a complementarity determining region of an antibody, a synthetic antibody or chimeric antibody construct which shares sufficient CDRs to retain functionally equivalent binding characteristics of an antibody that binds a desired cell surface receptor, a binding fragments produced by phage display, a lectin, a hormone, a growth factor, and a drug and fragments thereof.

12. The method according to claim 1, wherein said instrument individually measures said detectable signal for each test sample or control using a parameter selected from the group consisting of direct current, radio frequency current, light scatter, fluorescence, and combinations thereof.

13. The method according to claim 12, wherein said instrument measures light scatter and fluorescent emission of complexes of formed bodies to which are bound multiple first analytes and multiple first ligands labeled with said detectable markers.

14. The method according to claim 13, wherein said detectable marker is fluorescent.

15. The method according to claim 14, wherein the fluorescent marker is selected from the group consisting of phycobiliproteins and tandem dyes.

16. The method according to claim 15, wherein said phycobiliprotein is selected from the group consisting of phycocyanin, allaphycocyanin, allophycocyanin B, phycoerytbrin, R-phycoerythrin, fluorescein isothiocyanate, phycoerythrocyanin, phycoerythrin-texas red, PE-Cy7, allophycocyanin-Cy5, and allophycocyanin-Cy7.

17. The method according to claim 12, wherein said instrument is a flow cytometer.

18. The method according to claim 1, wherein at least said steps (e)–(h) are performed by a computer program.

19. The method according to claim 1, wherein said detectable signals are mean channel intensity values, and wherein step (e) further comprises analyzing a first linear-log graphical dependence curve formed by plotting said mean channel intensity values measured from each said test sample against a molar concentration of said unlabeled first ligand in each said test sample, a second linear-log graphical dependence curve formed by plotting said mean channel intensity values measured from each said control against a molar concentration of said labeled first ligand in each said control, and a third linear-log graphical dependence curve formed by plotting said mean channel intensity values measured from each said test sample against a molar concentration of total labeled first ligand and unlabeled first ligand in each said test sample.

20. The method according to claim 1, wherein said first analyte is a receptor; said formed bodies are cells having said receptors bound thereto; and said first soluble analyte is the same receptors shed from said cell 21. The method according to claim 20, wherein said concentration of soluble receptors in step (h) is calculated according to the formula: D×binding valence of the ligand, adjusted for volume.

22. A method of diagnosing a disease characterized by an altered level of soluble analyte in the blood of a mammal, said method comprising (a) analyzing the amount of soluble analyte by performing the steps of the method of claim 1, and (b) comparing the concentration of soluble analyte from said mammal's samples with known normal concentrations of soluble analyte in samples of healthy mammalian blood, wherein a difference between the concentration of said soluble analyte in said mammal's blood sample and said normal concentrations is indicative of disease.

23. A method of diagnosing a disease characterized by an altered level of soluble first receptors in the blood of a mammal, said method comprising
    (a) analyzing the amount of soluble receptor in said mammalian blood sample, wherein said analysis comprises the steps of the method of claim 20, and
    (b) comparing the concentration of soluble receptors from said mammal's blood samples with known normal concentrations of said soluble receptors in samples of healthy mammalian blood,
    wherein a difference between the concentration of said soluble receptors in said mammal's blood sample and said normal concentrations is indicative of disease.

* * * * *